US00PP17504P3

(12) United States Plant Patent
Maranto

(10) Patent No.: US PP17,504 P3
(45) Date of Patent: Mar. 20, 2007

(54) GRAPEVINE PLANT DENOMINATED 'BLANC SEEDLESS'

(50) Latin Name: *Vitis vinifera*
Varietal Denomination: Blanc Seedless

(75) Inventor: Joseph Maranto, Bakersfield, CA (US)

(73) Assignee: Anton G. Caratan, Delano, CA (US)

( * ) Notice: Subject to any disclaimer, the term of this patent is extended or adjusted under 35 U.S.C. 154(b) by 12 days.

(21) Appl. No.: 10/624,710

(22) Filed: Jul. 21, 2003

(65) Prior Publication Data

US 2005/0022277 P1 Jan. 27, 2005

(51) Int. Cl.
*A01H 5/00* (2006.01)

(52) U.S. Cl. ..... Plt./207

(58) Field of Classification Search ..... Plt./207
See application file for complete search history.

*Primary Examiner*—Kent Bell
(74) *Attorney, Agent, or Firm*—Worrel & Worrel

(57) ABSTRACT

A new and distinct variety of grapevine which is somewhat remotely similar to the 'Thompson Seedless' grapevine, but from which it is distinguished in a number of respects by producing fruit with a delayed period of cluster ripening occurring in mid October for harvesting and shipment, or approximately four weeks after the fruit produced by the 'Thompson Seedless' grapevine and wherein the fruit is large, having a mild flavor, a light green skin coloration and a firm, crisp flesh.

1 Drawing Sheet

Latin name of the genus and species of the plant claimed: *Vitis vinifera.*

BACKGROUND OF THE NEW VARIETY

The present invention relates to a new and distinct variety of grapevine, which will hereinafter be denominated varietally as the 'Blanc Seedless' grapevine, and, more particularly, to a grapevine which is large, vigorous and productive, the fruit of which is mature for commercial harvesting and shipment in mid October in the San Joaquin Valley of central California.

The 'Thompson Seedless' grapevine, particularly when viewed from a historical vantage point, is one of the most commercially successful grapevines to have been discovered and commercialized. The San Joaquin Valley of central California, one of the most productive areas of the world for grapevine borne crops, has seen plantings of many thousands of acres of this variety over many decades. In some respects, it is the commercial standard by which many other varieties are judged. Nonetheless, there have been many subsequently discovered, commercially successful varieties of grapevines.

With these considerations in mind, it is always a desire in experimentation to discover new grapevine varieties which have improved characteristics relative to prior successful varieties. For example, the objective may be to discover a new variety which has the attractive characteristics of the prior variety, but which may be distinct therefrom in certain respects, such as the ripening date. In this example, the extension of the market for such fruit resulting from the existence of a different ripening date enhances the market value of the fruit produced thereby, in some instances for both varieties.

The grapevine of the present invention has many of the attractive characteristics of prior commercially successful varieties, while possessing distinctive qualities which make it uniquely appealing.

ORIGIN AND ASEXUAL REPRODUCTION OF THE NEW VARIETY

The present variety of grapevine hereof, *Vitis vinifera,* was discovered by the inventor in a grapevine breeding program initiated in 1992 in a vineyard which is located near Delano, in San Joaquin Valley of central California. The grapevine of the present invention was discovered in a cross breeding of the 'Red Globe' grapevine (female) (U.S. Plant Pat. No. 4,787) and the 'Crimson' grapevine (male), both commercially successful varieties of grapevines producing red fruit and with complex parentage grown in California. Throughout the season, the newly discovered variety, evidenced that the fruit produced therefrom is seedless, and the grapevine slightly resembles a large 'Thompson Seedless' grapevine. However, the fruit produced thereby has a much later ripening date. The present variety has very distinctive quality characteristics, relative to other known varieties and can be distinguished therefrom in a number of other important respects which may be summarized in part as producing a table grape of outstanding size relative to other seedless varieties and with a delayed period of ripening.

In 1998, the present variety was successfully grafted, for asexual reproduction, on mature 'Thompson Seedless' grapevine root stock and planted in the aforesaid vineyard. The inventor monitored the asexually reproduced grapevines of the instant variety and confirmed that, in all respects, the asexually reproduced grapevines were identical to the original grapevine of the new variety.

SUMMARY OF THE NEW VARIETY

The grapevine denominated 'Blanc Seedless' is characterized by producing large, generally white, or light green, seedless berries which are ripe for commercial harvesting and shipment in approximately mid October in the San Joaquin Valley of central California. The new variety is, perhaps, most closely similar to the 'Thompson Seedless' grapevine, but is distinguished therefrom in a number of respects, including the aforementioned ripening date. The fruit is firm, has a mild flavor, good eating quality and an apparent resistance to adverse conditions.

BRIEF DESCRIPTION OF THE DRAWING

The drawing is a color photograph showing representative portions of the grapevine of the subject invention including a cluster of grapes with attached section of the cane or branch, and foliage disposed to show the under surface of the leaf thereof, a second leaf disposed to show the upper surface thereof, and two berries, or grapes, from the cluster, a first berry sectioned along the axis transverse to the longitudinal axis and laid open to expose the flesh and a second berry sectioned and laid open along the longitudinal axis to expose the flesh, together with a scale to indicate the relative sizes of the portions depicted in the photograph.

DETAILED DESCRIPTION

Referring more specifically to the botanical details of this new and distinct variety of grapevine, the following has been observed under the ecological conditions prevailing at the vineyard of origin which is located near Delano, Calif. All major color code designations are by reference to the *Dictionary of Color,* by Maerz and Paul. Common color names are also occasionally employed.

The variety of the subject invention was selected by the inventor from a progeny of two hundred twenty (220) seedlings planted in 1994 in a field in the Delano area of the San Joaquin Valley of California. The new variety was then asexually reproduced on 'Thompson Seedless' grapevine root stock from the original seedling in the spring of 1998 at the same location. The original disclosure of the asexually reproduced grapevine of the new variety was prepared in the spring of 2003.

VINE

Generally:

*Size.* —Large. Appearing as a bush. Typical observed plant height 5 feet to 6 feet and plant diameter 5 feet to 6 feet, both subject to pruning and training. Some of the canes extend to 2.5 meters (8 feet) and the canes can be trained on high trellises.

*Vigor.*—Vigorous. More vigorous than either parent. The canopy is thick.

*Productive capacity.*—Very productive with spur pruning. Tendency to produce a small secondary crop on current season's growth.

Trunk:

*Size.* —Slender. Long split straps. Typical and observed trunk diameter at one foot height from ground, 59 millimeters (2.3 inches).

*Color.*—Bark — Dark brown (8-E-11) — Medium brown under bark (7-C-12) India Tan.

*Canes.*—Medium length and width (16–20 nodes). Some canes are long to 2.5 meters (8 feet). The width at the 3$^{rd}$ node is 11 millimeters (0.4 feet).

*Mature canes.*—Color — Raw Sienna (13-L-10).

*Notes.*—Round, slightly enlarged. Lengths between the nodes is 76.2 millimeters (3 inches) to 127.0 millimeters (5 inches).

*Shoots.*—Size — Medium to long.

*Shoots.*—Length — 76.2 millimeters (3 inches) to 101.6 millimeters (4 inches). Shoot diameter 0.7 millimeters. Shoots are slightly colored, light green, with a glossy appearance.

*Shoots.*—Shape — Circular to slightly flat.

*Shoots.*—Contour — Smooth.

*Tendrils.*—Numbers — Few.

*Tendrils.*—Length — 101.6 millimeters (4 inches) to 203.2 millimeters (8 inches).

*Tendrils.*—Location — Discontinuous.

*Tendrils.*—Form — Bifurcated and trifurcated.

*Tendrils.*—Texture — Smooth.

*Buds.*—Shape — Conical, slightly pointed.

*Buds.*—Size — Medium. Average length 6 millimeters. Average width 6 millimeters.

*Buds.*—Fruitfulness — Base mostly fruitful.

*Bud break.*—Near Delano, in the San Joaquin Valley of central California, in the end of March.

LEAVES

*Size.*—Generally — Medium to large.

*Density.*—Heavy.

*Average length.*—Mature Leaf — 101.6 millimeters (4 inches) to 152.4 millimeters (6 inches).

*Average width.*—Mature Leaf — 127 millimeters (5 inches). Five lobes, basal lobe short, less prominent than laterals. Terminal teeth large in contrast with lateral teeth. Petiole sinus wide opened, "U" shaped, occasionally overlapping inferior sinuses. Inferior sinuses narrow.

*Texture.*—Upper Surface — Smooth.

*Texture.*—Lower Surface — Glabrous.

*Color.*—Dorsal — Dark green (24-L-7).

*Color.*—Ventral — Light green (23-L-7).

*Color.*—Leaf Vein — Midrib — Grape green (21-J-1).

*Petiole.*—Length — 76.2 millimeters (3 inches) to 127.0 millimeters (5 inches), round or flattened.

*Petiole diameter.* —Thin, 3 millimeters.

*Petiole color.*—Light green (23-L-7).

*Petiole sinus.*—Form — U shaped, lateral sinus occasionally overlapping.

*Lobe.*—Four pointed.

*Marginal form.*—Generally — Serrate, 10 to 14 per lobe.

*Teeth.*—Size — Irregular.

*Teeth.*—Number — 50 to 60.

*Teeth.*—Shape — Pointed.

INFLORESCENCE

*Size.*—Medium.

*Number borne per spur.*—Average two.

*Number borne per vine.*—30 to 35 (16 spurs).

FLOWERS

*Flowers.*—Location — (Node where fruit is produced.) — Usually 2$^{nd}$ to 4$^{th}$ node from the base on spur pruning. Flower, still closed, is pear shaped. Type — fertile. Pedicel — Adherence to berries — strong. Length — 7 millimeters to 8 millimeters. Number of clusters per vine 30 to 35. Microscopic bud examination indicates that six percent (6%) of the buds have double cluster primordia the size of peduncle. Medium length, 50 millimeters (2 inches). Average width 5 millimeters (3/16 inch).

*Date of bloom.*—May 5.

*Date of full bloom.*—May 10 to May 12.
*Date of visible berries set.*—May 18.
*Stamens.*—Upright or diverging. Numbers — 6. Stamens length 1.6 millimeters, filaments straight. Length of filaments — Average 2 millimeters. Petals and Sepals — Number 5. Sepals poorly developed.
*Color.*—light green — (22-L-4) Calla green. They are formed like a cap and at bloom the petals open from the bottom to the top from the pressure of the stamens and, after, stay at the top like an inverted cup and later drop.
*Pistils.*—Color — Light green (22-L-4) Calla green.
*Pistils.*—Number per flower — One small pistil which produces a liquid to hold pollen grains to favor germination.
*Amount of pollen.*—Abundant.
*Pollen.*—Color — yellow.

FRUIT

Maturity when described: Ripe for commercial harvesting and shipment approximately mid October near Delano, in the San Joaquin Valley of central California, about four weeks later than the 'Thompson Seedless' grapevine and two to three weeks later than 'Red Globe' grapevine (U.S. Plant Pat. No. 4,787) and 'Crimson' grapevine.
*Solids.*—Sugar — 19.0%.
*Acid.*—Percent titratable acidity 0.464% (At the end of September).
*Sugar/acid ratio.*—40.9.
*Juice PH.*—3.85 on Oct. 3, 2000.
*Seeds.*—None. Seedless.
*Capstem.*—Pedicel — Strong.
*Berry.*—Weight — 6 grams (0.21 ounces) to 8 grams (0.28 ounces).
*Juice color.*—Colorless.
Size:
*Cluster.*—Generally — Medium to large. Cluster size — Length from the point of attachment averages 240 millimeters (12 inches). Cluster size itself averages 8 inches in length.
*Cluster.*—Weight — Average one pound.
*Compactness.*—Loose to compact.
*Cluster.*—Form — Conical shouldered.
*Berry.*—Size — Medium to large.
*Berry.*—Form — Mostly uniform.
*Berry.*—Size — Dimensions Longitudinal Axis — 20 millimeters (0.8 inches) to 25 millimeters (1 inch).
*Berry.*—Size — Diameter Axis — 14 millimeters (0.56 inches) to 16 millimeters (0.64 inches).
*Berry.*—Numbers — 100 to 140 per cluster.
*Form.*—Ellipsoidal elongated.
Skin:
*Thickness.*—Smooth, thick and resistant to detachment.
*Texture.*—Firm.
*Tendency to crack.*—None.
*Color.*—Light green (21-K-2) and amber yellow (10-J-3) on exposed berries.
*Pulp.*—Adheres to skin.
*Lenticels.*—One small, round pore like in distal end.
Flesh:
*Flavor.*—Sweet, mild to neutral. Chalaza long and attached to vascular tissue.
*Texture.*—Crisp, firm.
*Color of flesh.*—Pale green.
*Eating quality.*—Good.
Use: Dessert.
Keeping quality: After two months in the storage, still in good appearance.
Resistance to disease: Unknown.
Resistance to: Cold, drought, heat and wind. The new variety is well adapted to the type of soil and climatic conditions of the central valley of California where most of the table grapes in California are grown. The minimum and maximum temperatures range from 25° Fahrenheit to 108° Fahrenheit. Late spring fronts are rare in the central valley of California.
Shipping and handling qualities: Untested.

Although the new variety of grapevine possesses the described characteristics noted above as a result of the growing conditions prevailing near Delano, in the central part of the San Joaquin Valley of California, it is to be understood that variations of the usual magnitude and characteristics incident to changes in growing conditions, irrigation, fertilization, pruning, pest control, climatic variations and the like are to be expected.

It is claimed:

1. A new and distinct variety of grapevine plant substantially as illustrated and described which is somewhat remotely similar to the 'Thompson Seedless' grapevine, but from which it is distinguished in a number of respects including by producing fruit which is mature for commercial harvesting and shipment approximately in mid October in the San Joaquin Valley of central California and which has firm, medium to large berries of light green skin coloration which are seedless and with a mild flavor and crisp flesh.

* * * * *

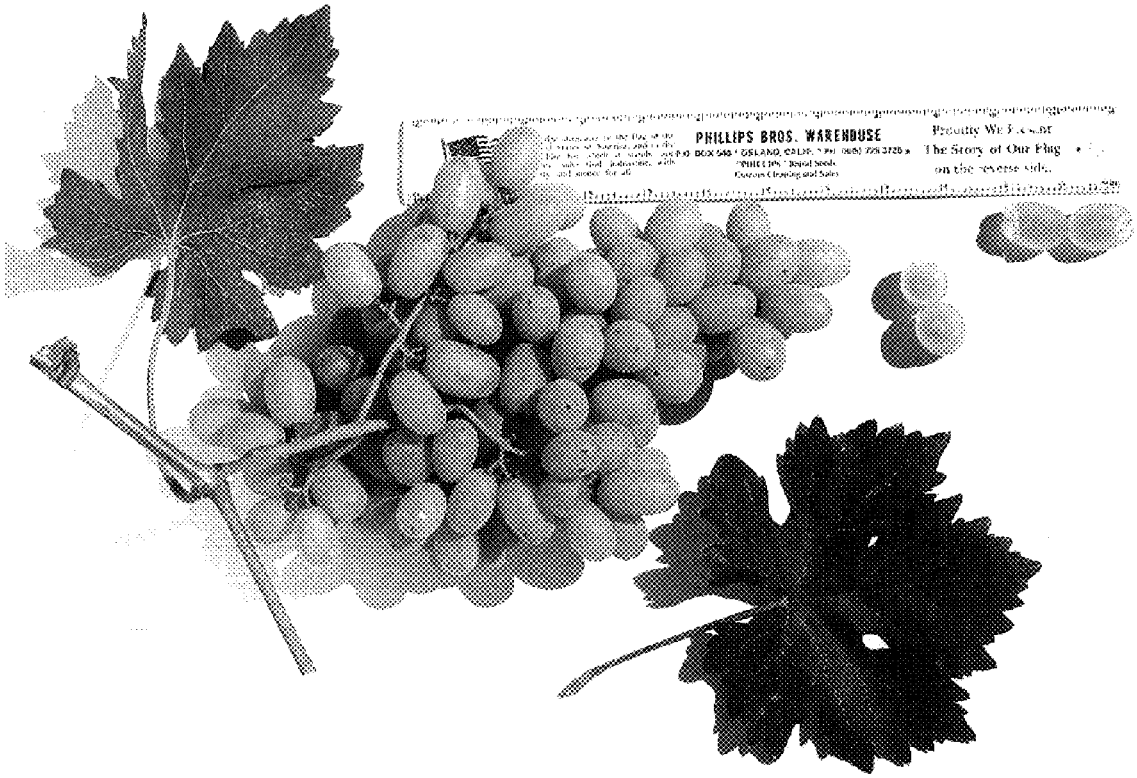
PHILLIPS BROS. WAREHOUSE
The Story of Our Flag
on the reverse side.